United States Patent [19]

Schwartz et al.

[11] Patent Number: 5,547,555

[45] Date of Patent: Aug. 20, 1996

[54] ELECTROCHEMICAL SENSOR CARTRIDGE

[75] Inventors: Jerome L. Schwartz; Michael D. Cabelli, both of Wilmington, Del.; John C. Silvia, Newtown; Craig D. T. Dahlin, Phoenixville, both of Pa.

[73] Assignee: Ohmicron Technology, Inc., Wilmington, Del.

[21] Appl. No.: 23,774

[22] Filed: Feb. 22, 1993

[51] Int. Cl.[6] ................................... G01N 27/26
[52] U.S. Cl. .......................... 204/418; 204/415; 204/412; 204/403; 422/82.05; 422/68.1; 422/82.01; 435/817; 435/287.1; 435/7.1; 435/4
[58] Field of Search ................. 204/418, 415, 204/412, 403; 422/82.05, 68.1, 82.01; 435/817, 288, 291, 7.1, 4

[56] References Cited

U.S. PATENT DOCUMENTS

| | | | |
|---|---|---|---|
| 4,560,534 | 12/1985 | Kung et al. | 422/68 |
| 4,568,445 | 2/1986 | Cates et al. | 204/415 |
| 4,717,673 | 1/1988 | Wrighton et al. | 436/68 |
| 4,721,601 | 1/1988 | Wrigthton et al. | 422/68 |
| 4,916,075 | 4/1990 | Malmros et al. | 435/291 |
| 4,929,313 | 5/1990 | Wrighton | 204/153.1 |
| 4,929,426 | 5/1990 | Bodai et al. | 422/63 |
| 4,963,245 | 10/1990 | Weetall | 204/403 |
| 5,001,048 | 3/1991 | Taylor et al. | 435/4 |
| 5,063,081 | 11/1991 | Cozzette et al. | 427/2 |
| 5,074,977 | 12/1991 | Cheung et al. | 204/153.1 |
| 5,098,545 | 3/1992 | Patko | 204/415 |
| 5,111,221 | 5/1992 | Fare et al. | 357/25 |
| 5,120,420 | 6/1992 | Nankai et al. | 204/403 |
| 5,145,645 | 9/1992 | Zakin et al. | 422/98 |

FOREIGN PATENT DOCUMENTS

| | | |
|---|---|---|
| 0158834 | 10/1985 | European Pat. Off. . |
| 20857755 | 3/1990 | Japan . |
| 2157646 | 6/1990 | Japan . |
| 2284496 | 11/1990 | Japan . |
| 3179248 | 8/1991 | Japan . |
| 2204408 | 11/1988 | United Kingdom . |
| 9109139 | 6/1991 | WIPO . |

Primary Examiner—Bruce F. Bell
Attorney, Agent, or Firm—Elman Wilf & Fried

[57] ABSTRACT

An electrochemical sensor cartridge with at least three reservoir cells, the floor of each cell in leakproof contact with the surface of an electrode assembly whose conductivity is affected by the presence of an analyte in that cell.

18 Claims, 11 Drawing Sheets

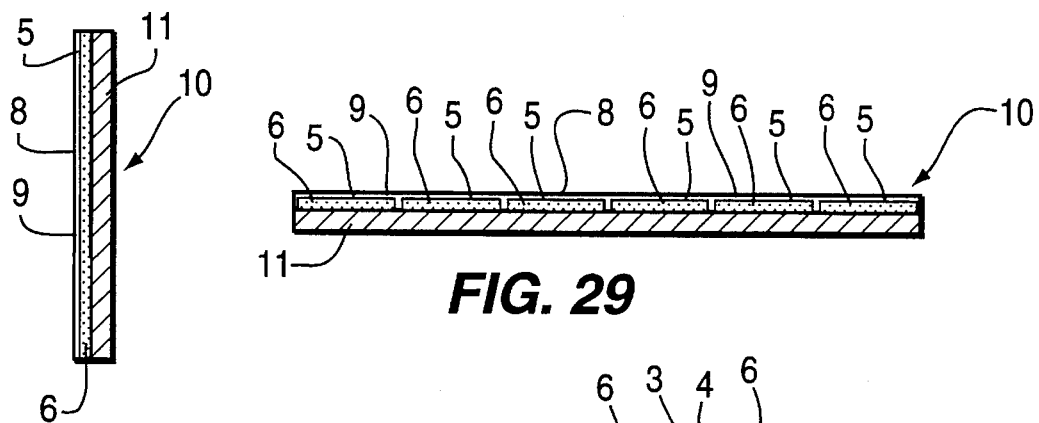
FIG. 28
FIG. 29
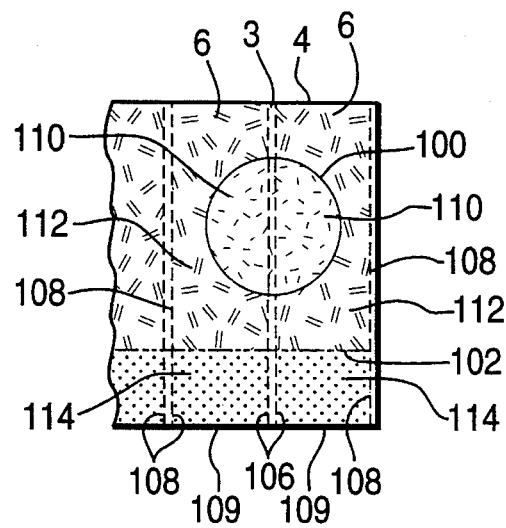
FIG. 30
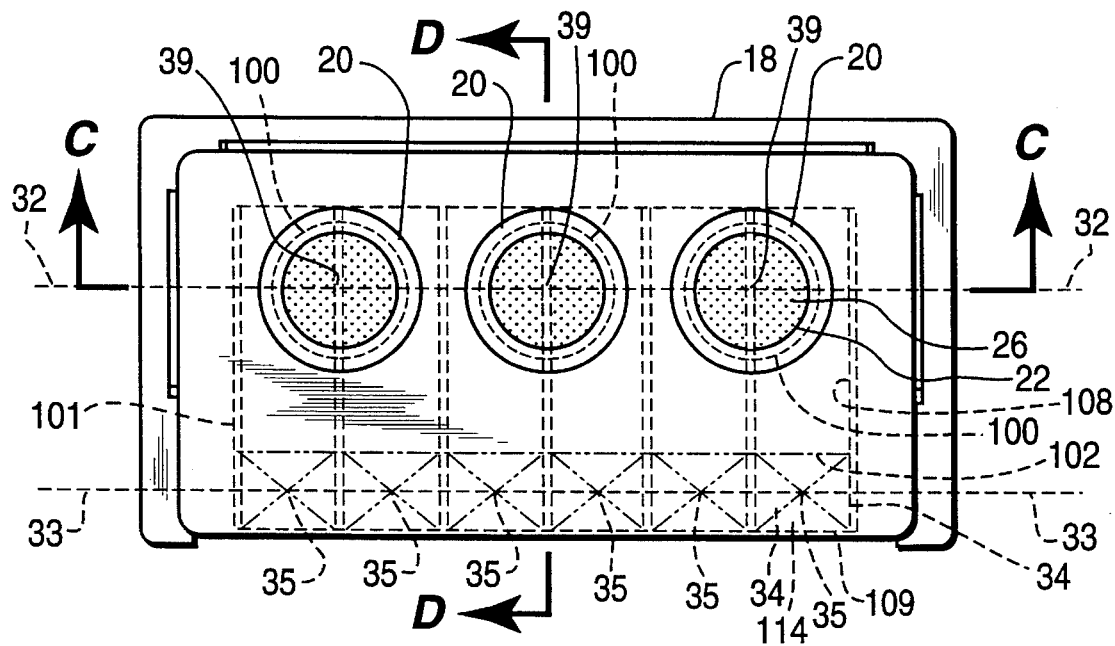
FIG. 31

5,547,555

ELECTROCHEMICAL SENSOR CARTRIDGE

FIELD OF THE INVENTION

The inventions relate to electrochemical sensor cartridges useful for detecting and quantifying an analyte in a sample of fluid.

BACKGROUND

Electrochemical sensor instruments can detect and quantify chemicals in fluids without the use of radioactive materials and, in contrast to colorimetric methods, even in the presence of color and/or turbidity. The general principle is to construct a sensor with an electroactive sensing element, one whose electroconductivity changes in response to the presence of the analyte of interest, either because the sensing element combines with the analyte or because the sensing element combines with a reaction product whose concentration is affected by the presence of the analyte.

It is advantageous for the electrochemical sensor instrument to have two separate components: a cartridge and an electronic instrumentation unit. The cartridge will have one or more cells for receiving fluid samples, an electroactive sensing element in each cell, and an electrical connection that, when the cartridge is placed in the instrumentation unit, connects the electroactive sensing element to the instrumentation unit.

Optimal use of sensors for environmental, agricultural, or medical diagnostic purposes requires that they meet minimum standards of accuracy and precision. Quantitative analysis involves a comparison between the electrical changes caused by the test sample and the electrical changes caused by at least one standard, such as a sample with known analyte concentration. Nevertheless, limitations on accuracy and precision occur in such comparisons. Sources of such variation include fluctuations in electroactive sensing element composition and dimensions that are inherent in the electrode manufacturing process. The present inventions deal with improvements in electrochemical sensor design that help to minimize the effects of such variations.

BRIEF SUMMARY OF THE INVENTION

One of the present inventions is an electrochemical sensor cartridge with at least three reservoirs or cells, the cells preferably in a linear array and preferably cylindrical in shape. Solutions of known analyte concentration can be added to two of the cells, and a solution of unknown analyte concentration can be added to a third cell. The invention improves accuracy, simplifies electrical circuit design, and decreases production cost. In a particularly useful embodiment, the cartridge can be easily assembled from as little as three light-weight parts.

BRIEF DESCRIPTION OF THE DRAWINGS

FIG. 28 is a side elevational view of the electrode assembly of FIG. 27.

FIG. 29 is a front elevational view of the electrode assembly of FIG. 27.

FIG. 30 is a top plan view of a portion of the electrode assembly of FIG. 27, with additional dashed lines to identify schematically various functional areas of the electrodes.

FIG. 31 is a plan view of the assembled cartridge of FIG. 2, lines are added to illustrate the drawing of parallel lines through the centers of the cell floors and the centers of the access electrodes.

DETAILED DESCRIPTION

GLOSSARY AND DISCUSSION OF TERMS USED

Figure 1:
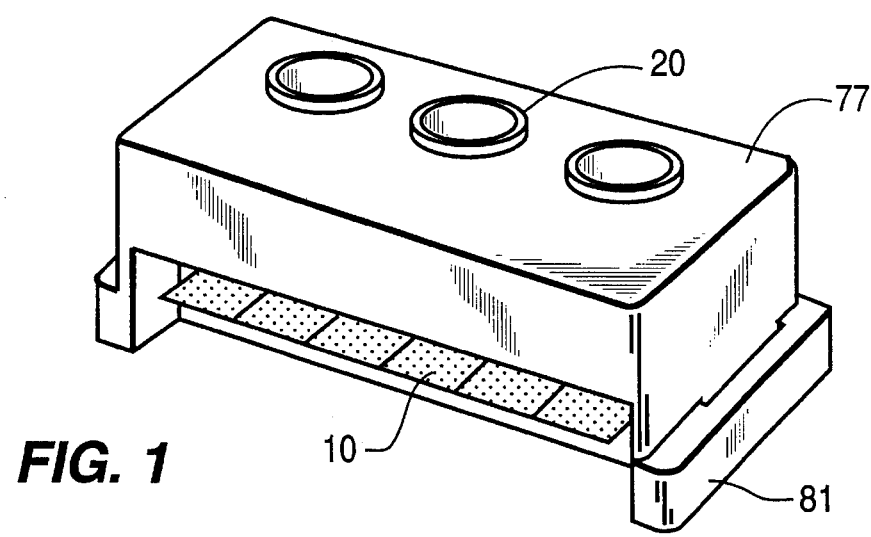
FIG. 1 is a perspective view of an assembled cartridge.

An "electroactive polymer" is one whose conductivity can be changed by oxidizing it or reducing it. Electroactive polymers and their mechanism of action are disclosed and discussed by M. G. Kanatzidis et al., *Chemical & Engineering News*, Dec. 3, 1990, pp. 36–54. For sensors, oxidative doping is the more frequently used mechanism to convert an electroactive polymer from a lower conducting to a higher conducting state. Reductive doping is also possible, however.

The spectrum of polymers that are electroactive is very broad. They include, but are not limited to, polyacetylene, polypyrrole, polythiophene, poly(3-alkylthiophene), polyphenylene sulfide, polyphenylene vinylene, polythienylene vinylene, polyphenylene, polyisothianaphthene, polyazulene, polyfuran, polyanaline, and derivatives of the foregoing.

An "electroactive sensing element" is pan of a sensor whose electrical properties change in response to the presence of an analyte. The change may due to the analyte interacting directly with the sensing element or due to the analyte triggering the production or diminution of a substance that interacts directly with the sensing element. Examples of sensing elements are those made of metal and those made of electroactive polymers.

An "analyte" is a substance that an analytical procedure seeks to detect and quantify. Some analytes (e.g., $Na^+$) can interact directly with a sensing element and cause detectable changes in that sensing element's electrical properties. Some analytes can be detected because they trigger or inhibit chemical or biochemical reactions that generate dopants (e.g., $I_3^-$) that effect electrical properties of sensing elements.

An "electronic instrumentation unit" is any measuring device that responds to changes in the electronic properties of the sensing element, cell electrode system, or the test solution in a cell; e.g., changes in resistance, capacitance, field strength, ionic conductivity, or solution impedance (impedimetry).

DISCUSSION OF THE INVENTION

In a general aspect, the invention is an electrochemical sensor cartridge comprising an electrode assembly and at least three hollow cells, each hollow cell comprised of a cell floor and a cell wall with a lower rim, wherein the cell floor is a portion of the electrode assembly top surface, wherein each said lower rim is in leak-proof contact with the outer perimeter of said cell floor. For each cell floor, the electrode assembly comprises an electroactive sensing element in contact with an electroconducting means accessible to an electrical contact external to the cartridge. Preferably, each electroconducting means comprises a cell electrode (especially a metal electrode), an electrical connector, and an access electrode. The electroactive sensing element is either in direct contact with or is part of the cell electrode, the connector is in direct contact with the cell and access electrodes, and the access electrode is sufficiently exposed so as to be able to make direct contact with an electrode or connector of an electronic instrumentation unit.

The electroactive sensing element may be part of the electrode itself, as when the sensing element is made of metal. Alternatively, the sensing element may be distinct from but in contact with the electrode, as when the sensing element is an electroactive polymer.

The hollow cell is preferably cylindrical in shape by virtue of the cell wall enclosing a hollow cylinder; in such a case the lower rim of the wall will be in the shape of a circle. The hollow cell can, however, have other shapes so that the lower rim of the wall will have a rectangular, square, triangular, hexagonal, elliptical, or other shape.

The cartridge will preferably have at least one linear array of cells with at least three cells in such a linear array. Of course, the cartridge may have more than one linear array. If there are two or more such arrays, the arrays may be parallel to each other. Alternatively, the linear arrays may be at right angles to each other, form a crossing pattern, form a square pattern with each linear array making up one side of the square, form a rectangular array with each linear array making up one side of the rectangle, and similarly form a triangular or hexagonal or other shape. There are many variations in which linear arrays can be arranged.

The access electrodes of the cartridge also preferably form a linear array, especially one parallel to the linear array of cylinders. Alternatively phrased, a line drawn through the midpoints of the cell floors is preferably parallel to a line drawn through the midpoints (e.g., the center of a circle, the intersection of two diagonals of a rectangle) of the access electrodes.

Generally, the axis of symmetry of each cylinder will be at right angles to the top surface of the electrode assembly.

In a preferred embodiment, the electrode assembly comprises a set of parallel metal strips, each metal strip separated from the others. Each metal strip comprises a first region that serves as a cell electrode, a second region that serves as a connector, and a third region that serves as an access electrode. The first region is contiguous with the second region, the second region contiguous with the third region.

In one preferred set of embodiments, each metal strip will be a thin layer of metal deposited on a relatively thick layer of nonconducting material. In a subset of those embodiments, each metal strip is overlaid with a thin layer of electroactive polymer. Such a layer may form a top layer to the entire assembly, and extend down into the spaces that separate the metal strips. Alternatively, the thin layer may not cover the entire assembly but, for example, only cover the electrodes.

The presence of at least three cells allows one cell for the addition of a first standard (e.g., an analyte sample of known concentration), a second cell for the addition of a second analyte standard (preferably an analyte sample with a second known concentration, possibly zero), and a third cell (generally located between the other two) for the addition of a test sample with an unknown analyte concentration. The test sample will normally be a solution and may be aqueous or nonaqueous. As a result, the user can determine, with greater accuracy than if there was only one cell per sensor, whether the concentration of the analyte in the test sample falls between those of the two standards. The determination is essentially independent of batch-to-batch variations in the electroactive polymer solution that is used to coat the electrodes, because the entire electrode assembly will be made from the same batch. If there are, for example, only three cells, the cells can be grouped together so that their floors are localized within a smaller area of the electrode assembly top surface than if four cells of the same size were used. Frequently, the smaller the area of the assembly surface that can localize all the cell floors, the less the floor-to-floor variation in floor composition (e.g., polymer thickness). When the cells are localized in a linear array, there are frequently less variations in floor-to-floor composition than if other arrays. The use of a linear array of cells optimizes the size of the cartridge necessary to house the three cells, thereby saving materials and space. Also, the geometry of the arrangement simplifies the design and manufacture of the electrode assembly.

In one set of embodiments of the invention, the assembly contributes two cell electrodes to each cell, such that the conductivity between those the two electrodes is dependent on the conductivity of the electroactive sensing element whose conductivity is affected either by the presence of analyte or compounds whose concentration is affected by the presence of analyte.

Preferably, the cartridge further comprises an overhang or canopy that covers an area above the exposed access electrodes so as to protect those electrodes from scratching and to prevent a drop of fluid from inadvertently falling onto those exposed electrodes. The lower edge of the overhang can be designed so that a drop that runs down along the overhang's outside surface to the overhang's lower edge will tend to fall from the outside of the overhang edge rather than that edge's midpoint or inside.

Additionally, the overhang surface functions as means of correctly aligning the cartridge at its correct location on the instrumentation unit into which the cartridge is docked for conductivity measurements.

The electrode assembly is preferably a flexible thin film. If it comprises an electroactive polymer, the choice of polymer will depend on the particular type of assay used to detect the analyte.

In one set of embodiments of the invention, a specific binding entity is physically or chemically attached to the floor, wall, or other component of the cell. Such other components include porous membranes or meshes, and objects that fit into the cell but do not take up all of the space in the cell. The specific binding entity can be an ionophore, antibody, lectin, antigen, hapten, biotin, avidin, streptavidin, enzyme or any other compound with selectivity as to its binding ability.

The cell may have a third electrode which can function as a reference, base, chemical potential-measuring, or voltage normalization electrode. That third electrode can be, but must not necessarily be, part of the electrode assembly. It may, for example, enter the cell through the top of the cell.

A preferred embodiment of the cartridge is one that is constructed from two plastic molded parts and a flat sheet electrode assembly by snapping or screwing the parts together. In one variation of such a cartridge, a pressure pad is added between the electrode assembly and the base unit. In another variation, the pressure pad lies on the electrode assembly. In the latter variation, the pressure pad has an aperture located over each portion of the electrode assembly that functions as a cell floor. The aperture may be of a size such that the lower rim of the cell wall actually makes contact with the top of the pressure pad; in such a case the inside of rim of each pressure pad aperture is effectively an extension of the lower end of the cell wall and functions as a sealing means to prevent leaking.

A cartridge that is constructed from a small number of plastic molded parts and can be snapped or screwed together is commercially attractive because its molded parts can be made relatively inexpensively. Also they are of light weight. In preferred versions, the outside shell or housing is molded in two different pieces (possibly hinged together), a base unit upon which the electrode assembly rests and a cover unit which fits over the base and electrode assembly and snaps or screws into the base.

The cover unit comprises the cylinders and, if present, the overhang. The base unit comprises a platform upon which the electrode assembly is placed and positioning means, such as a wall that allows accurate positioning of the electrode assembly. It will preferably have alignment means, such as parallel edges that allow the base (and also the fully assembled cartridge) to fit into an electronic instrumentation unit such that the electrodes will make proper contact with that unit's electrodes or connectors.

A cartridge with a cover unit and a base unit must further comprise a two-component securing means to hold the two units together: one protruding securing component (e.g., a screw or latch), and one receiving securing component that has an opening into or through which the protruding latch component fits. Generally, the receiving securing component must undergo some deformation to receive the protruding securing component; once having received that protruding component, it must undergo deformation again for that protruding component to be removed. If the protruding component is be part of the cover unit, the receiving component is part of the base unit. Conversely, if the protruding component is part of the base unit, the receiving component is part of the cover unit.

Formation of the electrode assembly

Electrodes can, for example, be fabricated by sputter-deposition of metal (e.g., to a thickness of 40 to 120 nm, but preferably about 80 nm, for platinum) in high-vacuum onto polyester film rolls. The metal is pattern-defined using modified lithographic techniques in which a water soluble paste is applied to areas which ultimately are to be free of metal, dried, and is then washed out along with its metal coating following the deposition process. This results in a parallel array of metal electrode strips and spacings. In a preferred embodiment, electrode strip widths (0.68 cm) and spacings (0.05 cm) are patterned to be on-center with standard electrical connectors in an electronic instrumentation unit.

Using the above principles, one can make the assembly by first preparing a thin sheet (e.g., 0.005 in. thick) of a flexible nonconducting material such as polyester (ICI-ST507 heat stabilized PET) with a silk-screen image of the desired line pattern comprising a water soluble paste, and then sputtering a metal pattern on it (e.g. platinum, gold, palladium, or iridium, but less expensive metals such as aluminum, copper, nickel, or zinc, may also be adequate; a bilayer with an expensive metal layered over a less expensive metal is also possible), using sputtering or other conventional techniques. Alternative methods include, but are not limited to, ion beam deposition and evaporation.

If it is desired to have an electroactive polymer layer, then in a subsequent step in the assembly manufacturing process, the assembly is overlaid with a coating of an electroctive polymer, according to a method appropriate for the polymer of choice. Possible methods include cast coating, spin coating, gravure, slot coating, and dip coating.

Electrosensor cartridge

Figure 7:
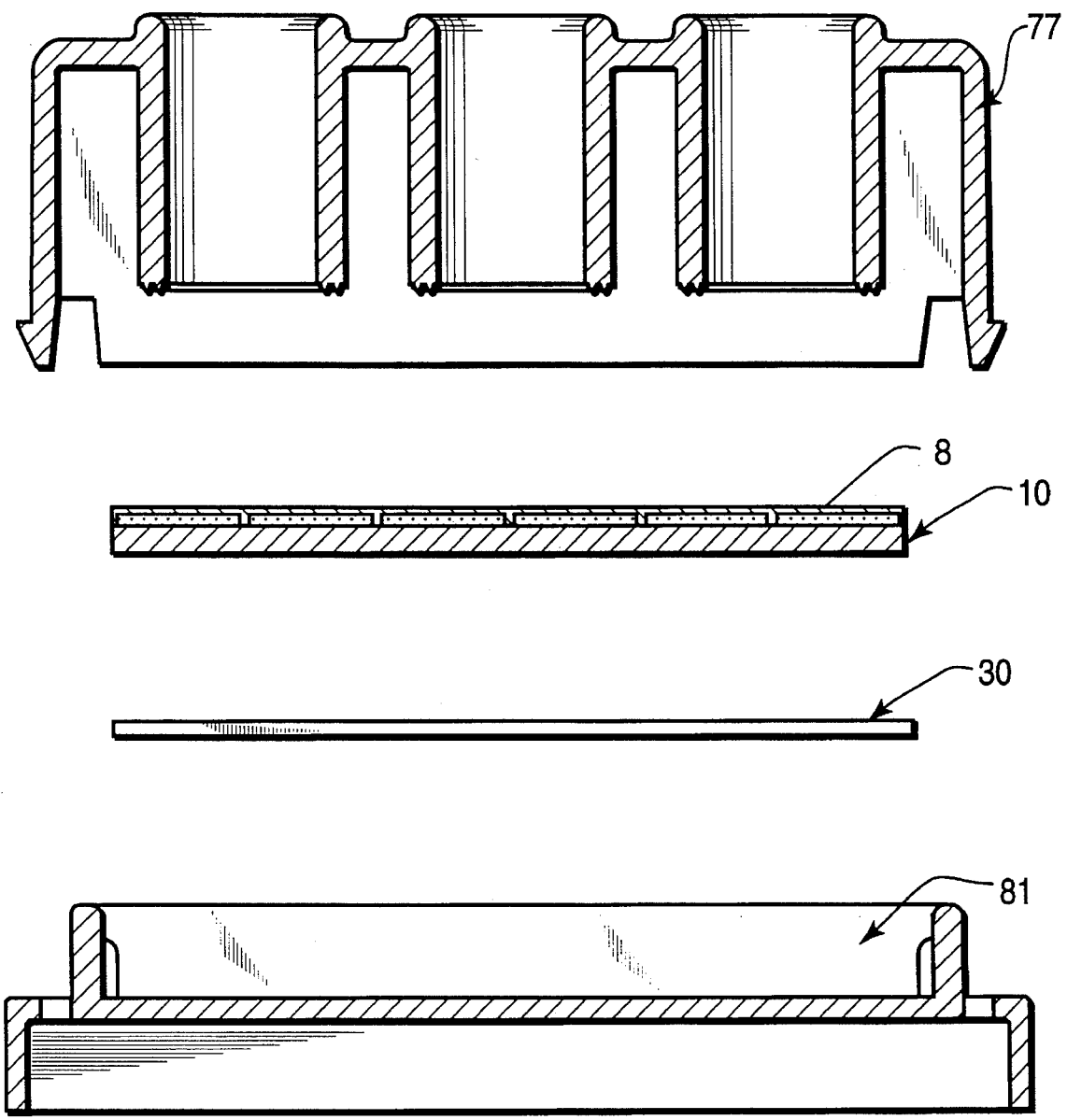
FIG. 7 is an exploded cross-sectional view of the assembled cartridge of FIG. 2 taken along the C—C axis of FIG. 2.

FIG. 1 is a perspective view of an assembled cartridge. FIG. 7 is an exploded cross-sectional view that illustrates that the cartridge is made of four parts: a cover unit (77), a base unit (81), a flat electrode assembly (10) and a pressure pad (30).

It will be evident from the dimensions cited below that the pressure pad (e.g. 0.079 cm. thick) and especially the electrode assembly (about 0.0127 cm., almost all of it due to the nonconductive film that is the bottom layer of the electrode) are very thin. In many of the drawings, the thickness of the pad and the electrode assembly are drawn disproportionately large (for comparison, consider that the cell diameter in the example is about 0.80 cm.) so as to assist the reader in visualizing the cartridge's construction. Similarly, the thickness of the electroactive polymer layer and the thickness of the metal electrodes are drawn disproportionately large compared to the thickness of the nonconductive film that forms the bottom layer. For example, with a nonconductive film that is 0.0127 cm. thick, a metal electrode of 40 to 120 nm thickness is usually used and, although the thickness of the electroactive polymer layer will depend on the particular application, it will frequently be less than 60 nm.

The cover unit and the base unit must be secured to each other so as to maintain the integrity of the cartridges, including the electrode assembly. The cover unit can be secured to the base unit by securing means that will frequently be a two-component securing means: a protruding securing component and a receiving securing component that has an opening into or through which the protruding component fits. The protruding component can, for example, be a latch component (as in the Figures), or a screw component. If it is a screw (not shown here), and the base unit has a screw receiving means (e.g., a threaded opening), then the cover unit will have to have an opening or aperture through which the screw can pass. Conversely, if the cover unit has a screw receiving means, then the base unit will have to have an opening or aperture through which the screw can pass.

The securing means provide a mechanism not only for holding the assembly together but also for exerting pressure against the electrode assembly so that it cannot easily be slid out. The pressure is effected by a tightening of the screws or a securing of the latch. Nevertheless, it is possible to design the shape of the electrode assembly so that such forces are not necessary to provide the resistance to electrode sliding. For example, the shape of the electrode assembly, instead of being rectangular, can be modified so that it conforms to the shape of the entire platform area. Such a shape would have indentations in the side edges of the electrode assembly, in order that the assembly can fit over the nubs. It would not then be possible to accidentally slide the electrode assembly out of the cartridge, because the presence of the nubs would prevent the electrode assembly from being slid out of the cartridge. A similar anti-sliding effect can be achieved by pin holes in the assembly, the pattern of holes being the same as a pattern of pins on the base unit; the pin holes would fit over the pins, and the electrode assembly would sit on the platform. The pins would prevent the assembly from sliding out.

Figure 2:
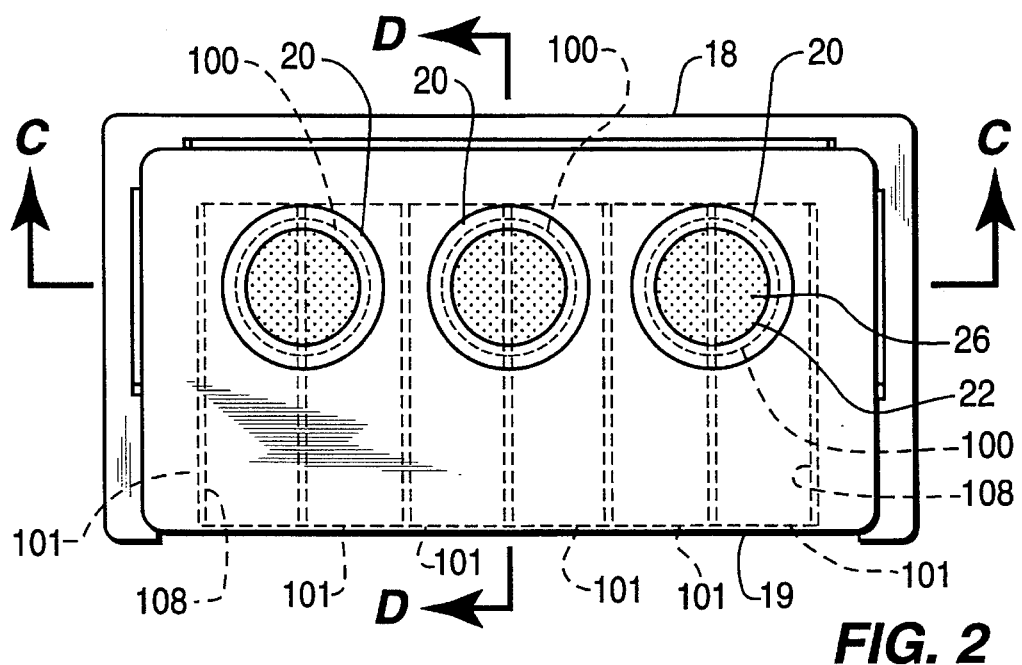
FIG. 2 is a top plan view of an assembled cartridge.

FIGS. 1, 2 through 6, 7, 8, 9, and 10, show various views of an assembled cartridge, illustrating the relationships of the cover unit (77), base unit (81), electrode assembly (10) and pressure pad (30). FIG. 2 is a top plan view of the assembled electrochemical sensor cartridge showing the top rims (20) of three hollow cylinders, as well as the positions of the inner wall surface (22) of each of those cylinders. (The cylinders are of identical construction and, although the rims are each marked with the number 20, in some Figures a structural element common to all the cylinders may actually be marked on only one cylinder, in order to make a drawing less crowded.) The back edge of the assembled unit (18) and the front edge (19) are also indicated. In FIG. 2, selected internal features of the cartridge, including the electrode assembly perimeter (101), are shown as dotted lines.

Also evident in FIG. 2 is the floor (26) of each cylinder. Each floor (26) is the circular area, on the electrode assembly top surface, circumscribed by a contact line (denoted by the number, 100) of the cylinder with that surface; that contact line defines the outer perimeter of the cell floor. The contact line is better understood by also considering the structure of the electrode assembly as depicted in FIGS. 27 through 29 and by examination of FIG. 30.

Figure 27:
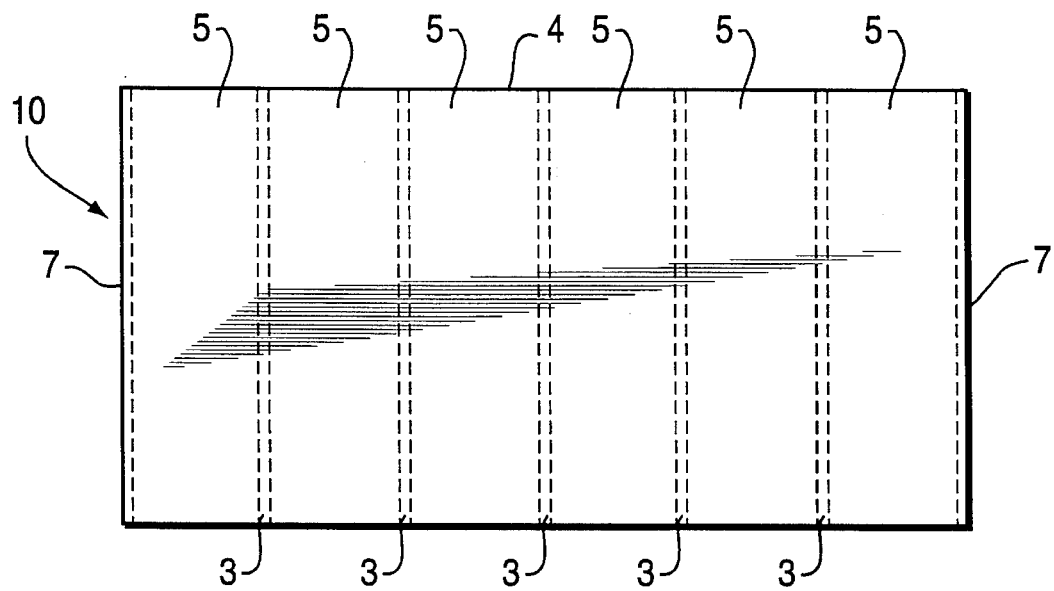
FIG. 27 is a top plan view of an electrode assembly.

FIG. 27 is a top plan view of an electrode assembly (10) that forms part of the electrosensor cartridge. FIGS. 29 and 28 show front elevational and side elevational views of the electrode assembly, respectively. The upper surface (8) of the assembly is an electroactive polymer film, such as polyacetylene, polypyrrole, polythiophene, poly(3-alkylthiophene), polyphenylene sulfide, polyphenylene vinylene, polythienylene vinylene, polyphenylene, polyisothianaphthene, polyazulene, polyfuran, polyanaline, or a derivative thereof. Under this film lie six metal strips (denoted by the number, 6) each of which has an upper surface (5). The metal strips lie on a nonconductive support sheet (11), and are separated by a separator strip (3) of electroactive polymer. The support sheet can be flexible (e.g., a polyester) or nonflexible (e.g., glass). If desired, binding substances such as antibodies may be physically or chemically attached to the surface of the polymer layer.

Figure 22:
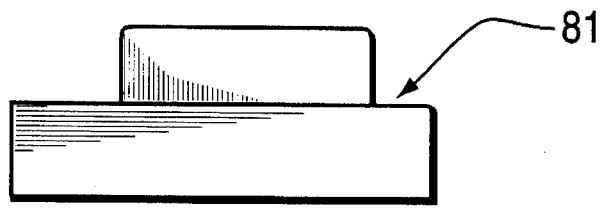
FIG. 22 is a side elevational view of the base unit of FIG. 20.
Figure 23:
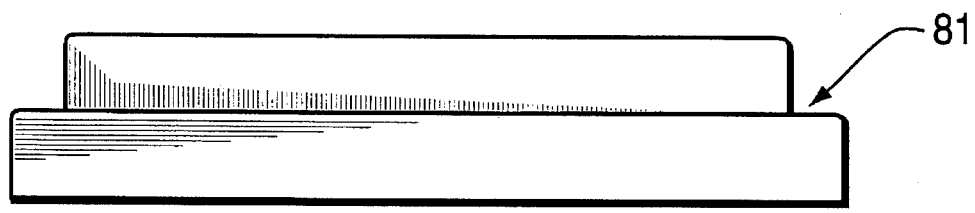
FIG. 23 is a back elevational view of the base unit of FIG. 20.
Figure 24:
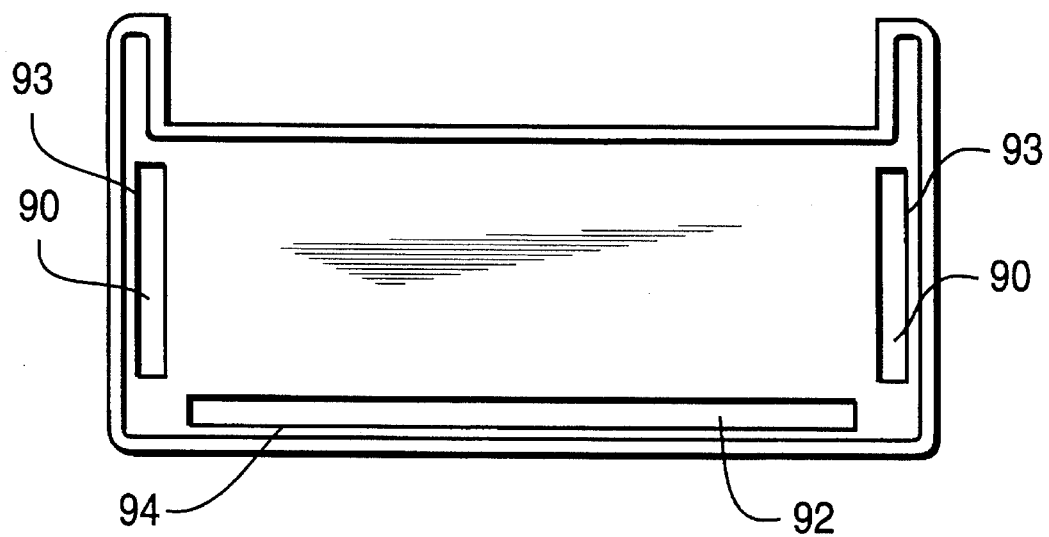
FIG. 24 is bottom plan view of the base unit of FIG. 20.

FIG. 30 shows in schematic fashion how a metal electrode strip (6) can be considered to be divided into functional segments: a cell electrode (110), an electrical connector (112), and an access electrode (114). The cell electrode is a segment whose outer perimeter is defined by the inner front-to-back edge (106) of an electrode strip (6) and the contact line (100) between a cylinder and the upper electrode assembly surface (8); denoted in FIGS. 6, 22, and 23 of that electrode. The electrical connector in the figure here is a segment whose perimeter is defined by the contact line (100) between a cylinder and the upper surface of an electrode assembly, by the inner front-to-back edge (106) of the electrode strip, by the outer front-to-back edge (108) of the electrode strip, by the contact line (102) between the divider wall lower edge (58); denoted in FIGS. 10, 15 and 16 and the upper assembly surface, and by the back edge of the electrode and electrode assembly (4). The access electrode (114) in the Figures here is a segment whose perimeter is defined by the front end (109) of an electrode strip (6), by the contact line (102) between the divider wall (58); denoted in FIGS. 10, 15 and 16 and the electrode assembly upper surface (8); denoted in FIGS. 7, 28, and 29, by the inner front-to-back edge (106) of the electrode strips, and by the outer front-to-back edge (108) of the electrode strips.

The contact line (100) defines the points at which the cylinder makes contact with the surface (see FIG. 30). When there are two or more such lines, such as those corresponding to the inner (70); denoted in FIGS. 15 and 17 and outer (72); denoted in FIGS. 15 and 17 lower rims of the cylinder (see FIGS. 15, 17, and 18), the contact line that defines the floor is the innermost circular contact line. It follows that the diameter of the floor will depend on how the cylinder contacts the electrode assembly top surface. If the cylinder contacts that surface without any substantial pressure being applied, then only the lowest edge (73) of the inner rim of the cylinder will be the cylinder portion that makes contact with the assembly surface (8); denoted in FIGS. 7, 28 and 29; as a result, that inner ridge will be the cylinder portion that circumscribes the cylinder floor. On the other hand, if the cylinder contacts that surface with pressure applied, the cylinder rims (70); denoted in FIGS. 15 and 17 and (72); denoted in FIGS. 15, 17 or the surface (8); denoted in FIGS. 7, 28 and 29 may deform slightly so that the contact line is a circle that lies on the cylinder rim somewhere between the inner cylinder edge (74); denoted in FIG. 17 and the lower edge (73); denoted in FIG. 17 of the inner rim.

In the Example in the figures, the cells form a linear array, for example, a straight line (32) can be drawn through the centers (39) of their floors. (See FIG. 31, which includes some elements from both FIGS. 2 and 30.) Furthermore, it is evident from FIG. 31 that the access electrodes (114) will also form a linear array: a straight line (33) may be drawn through their centers (35) (each access electrode center (35) is defined by the intersection of two diagonals (34) drawn on the access electrode (114).) Furthermore the linear array of cells is parallel to the linear array of access electrodes: line 32 is parallel to line 33. That parallel relationship simplifies the production and design of the electrode assembly: a large sheet with dozens of parallel metal strips. optinally polymer-coated, may be made and then cut into individual electrode assemblies. Also the cell-to-access electrode distances will be the same for all cells, simplifying the metal pattern design.

Figure 3:
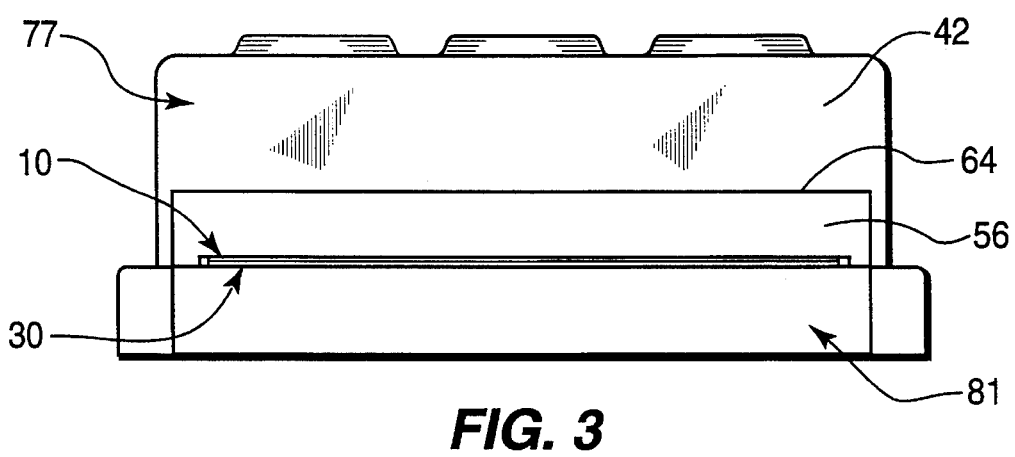
FIG. 3 is a front elevational view of the assembled cartridge of FIG. 2.
Figure 4:
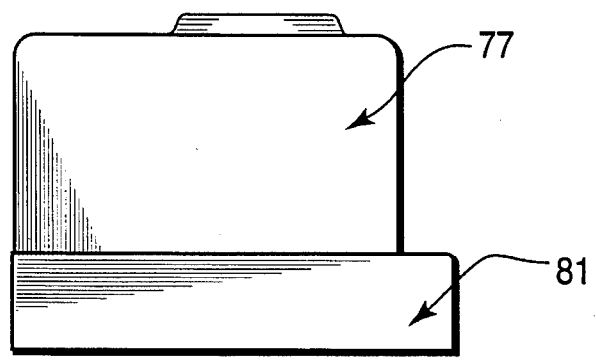
FIG. 4 is a side elevational view of the assembled cartridge of FIG. 2.
Figure 5:
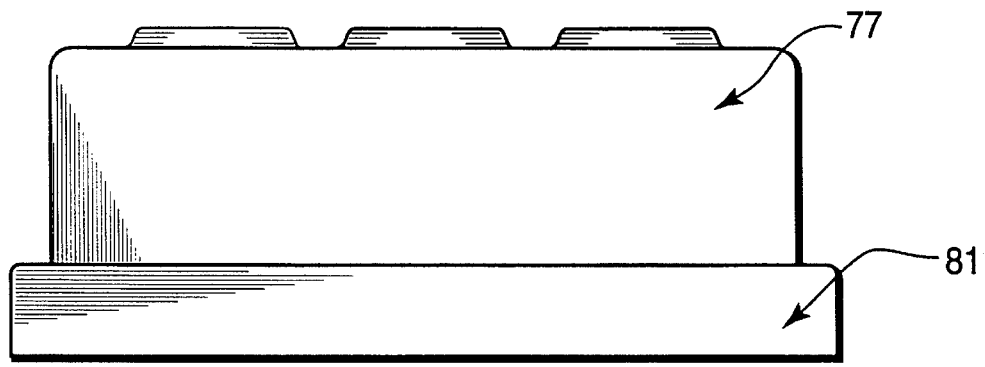
FIG. 5 is a back elevational view of the assembled cartridge of FIG. 2.
Figure 12:
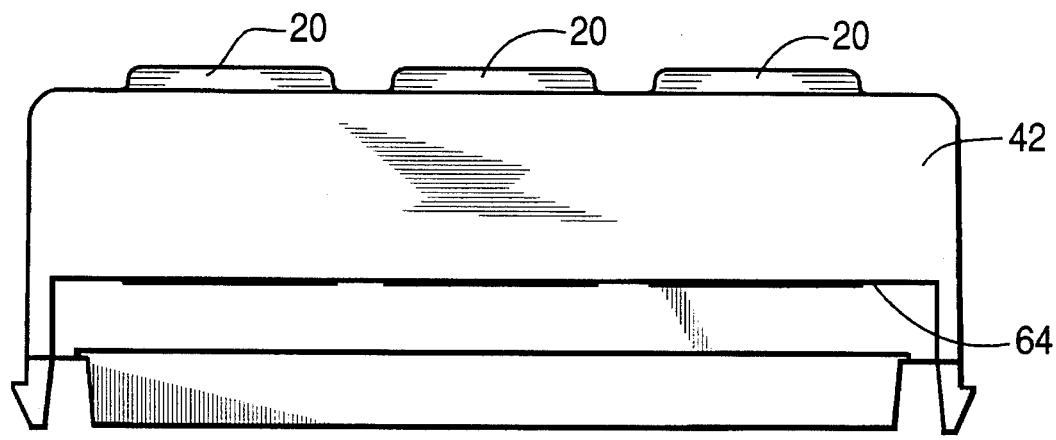
FIG. 12 is a front elevational view of the cover unit of FIG. 11.
Figure 13:
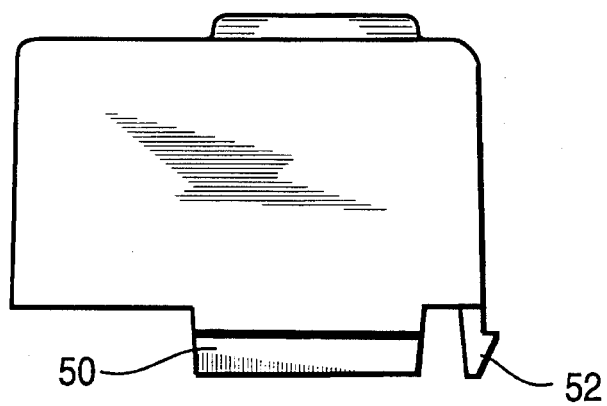
FIG. 13 is a side elevational view of the cover unit of FIG. 11.
Figure 14:
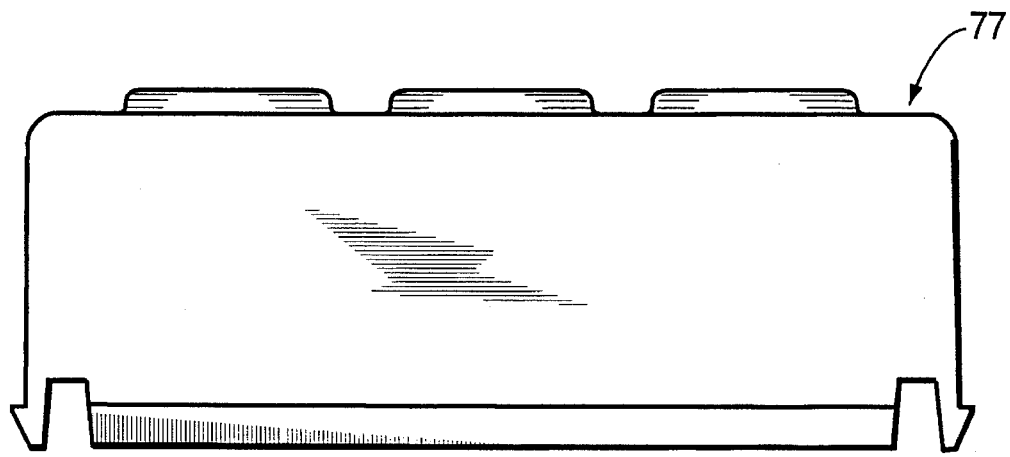
FIG. 14 is a back elevational view of the cover unit of FIG. 11.

FIGS. 3 through 5 are front, side, and back elevational views of the assembled cartridge, respectively. The front elevational view shows the front surface (42); denoted in FIGS. 3, 12 and 16 of the hanging segment of that overhang as well as the drop-repellant lower edge (63); denoted in FIGS. 15 and 16 of that overhang. The lower edge (63); denoted in FIG. 16 has a rounded inner edge (65); denoted in FIG. 16 and a sharp outer edge (64); denoted in FIGS. 3, 6, 12 and 16; that arrangement results in a drop accumulating on the outer, not the inner, edge.

Figure 6:
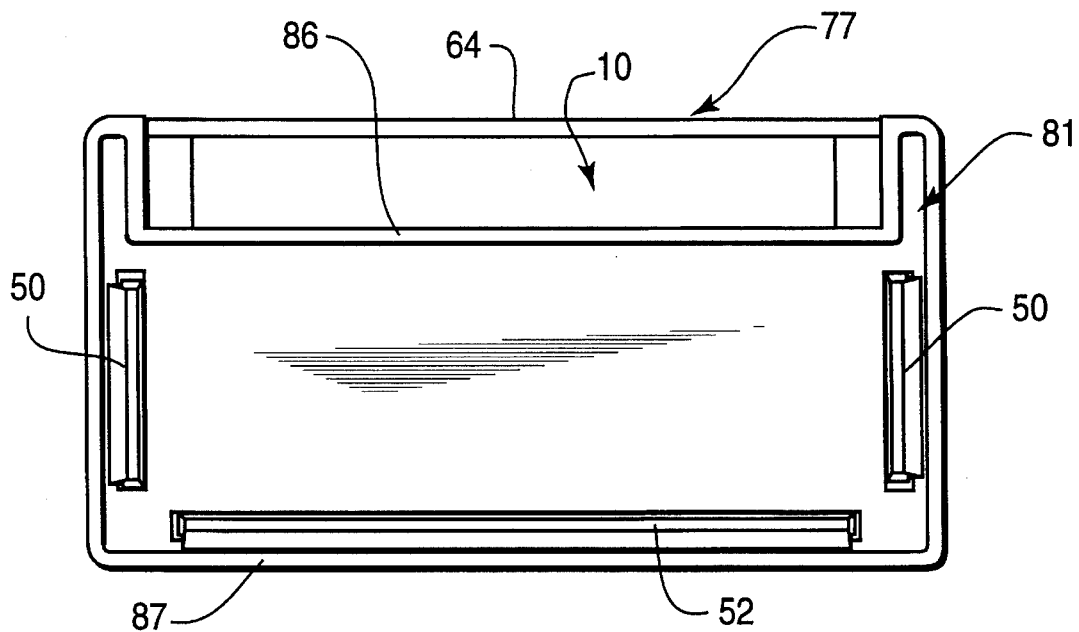
FIG. 6 is bottom plan view of the assembled cartridge of FIG. 2.

FIG. 6 is a bottom plan view of the assembled cartridge. The side protruding latch component (50) and the back protruding latch component (52) are visible.

Figure 9:
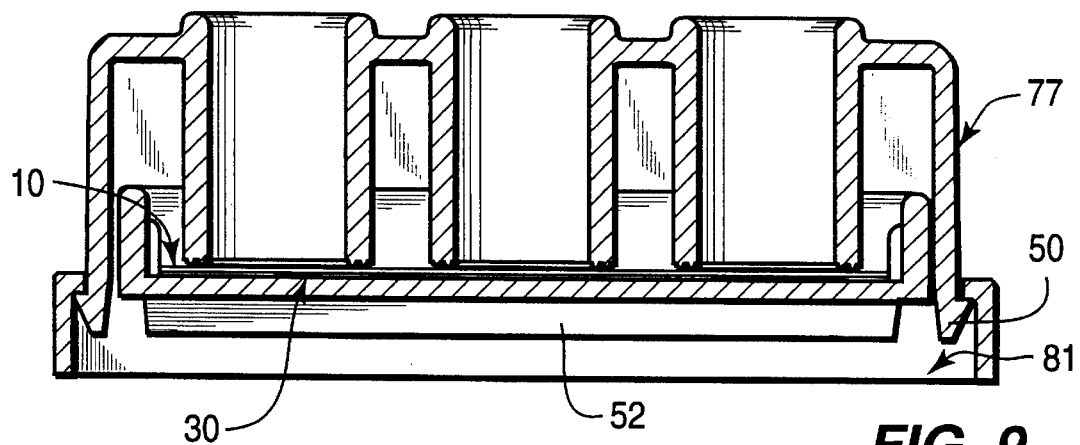
FIG. 9 is a cross-sectional view taken along axis C—C in FIG. 2.

FIG. 9 is a cross-sectional view of the assembled cartridge (taken along line C—C in FIG. 2). The fine structure of the electrode element, visible in the side elevational view of the cartridge has been omitted here.

Figure 10:
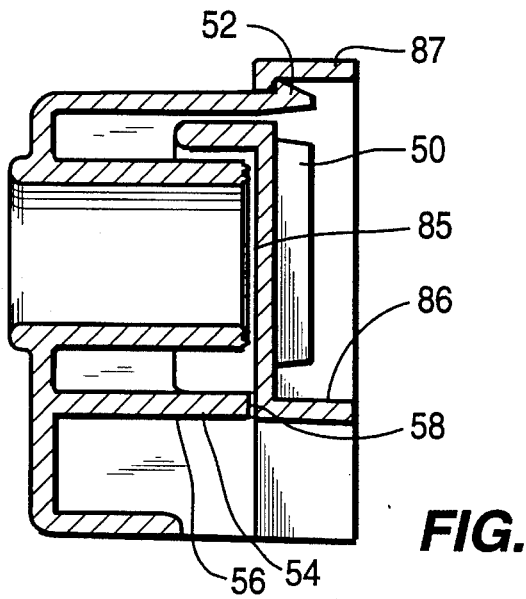
FIG. 10 is a cross-sectional view taken along axis D—D in FIG. 2, except that the electrode assembly and the pressure pad are not shown.

FIG. 10 is a cross-sectional view of the assembled cartridge (taken along line D—D in FIG. 2) exxcept that the electrod assembly and the pressure pad have been omitted. This view shows how a divider wall (54) whose outer surface (56) is at least partially visible in FIG. 3, the front elevational view of the assembled cartridge. Optimally, the lower edge (58) of the divider wall makes essentially continuous contact with the top surface of the electrode (8); denoted in FIGS. 7, 28 and 29, thereby helping to keep that electrode flat. The cover segment (59); denoted in FIG. 16 of the overhang and the "hanging section" (61) of the overhang are contiguous with each other and together comprise the overhang.

The access electrode region represents the area available to function as an access electrode for an electronic instrumentation unit; the electrodes or connector of the instrument unit may only in fact cover a portion of the access electrode region, a situation that would still leave the cartridge functional. The area available for functioning as an access electrode is limited by the presence of the divider wall of the cover unit. If the height of that wall is reduced, it would be possible to utilize some of the region, now designated as a connector region, as an access electrode.

If the manufacturing process results in polymer-coated electrode then, when the access electrode makes contact with the electrode of the measuring instrument, the microscopically thin layer (9); denoted in FIGS. 28 and 29 of conducting polymer covering the access electrode is removed.

Figure 19:
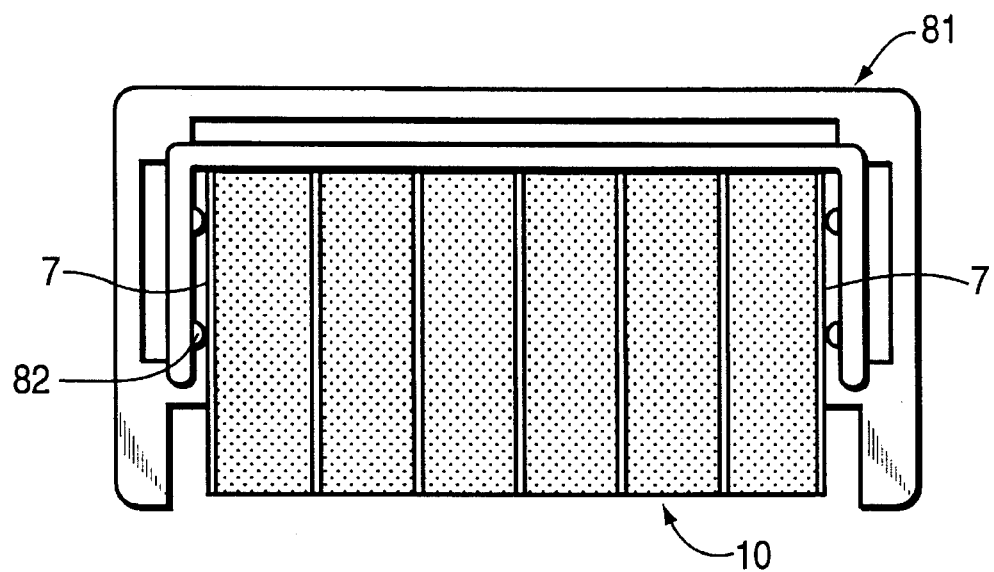
FIG. 19 is a top plan view of an electrode assembly lying on top of a pressure pad that lies on the platform of a base unit.
Figure 20:
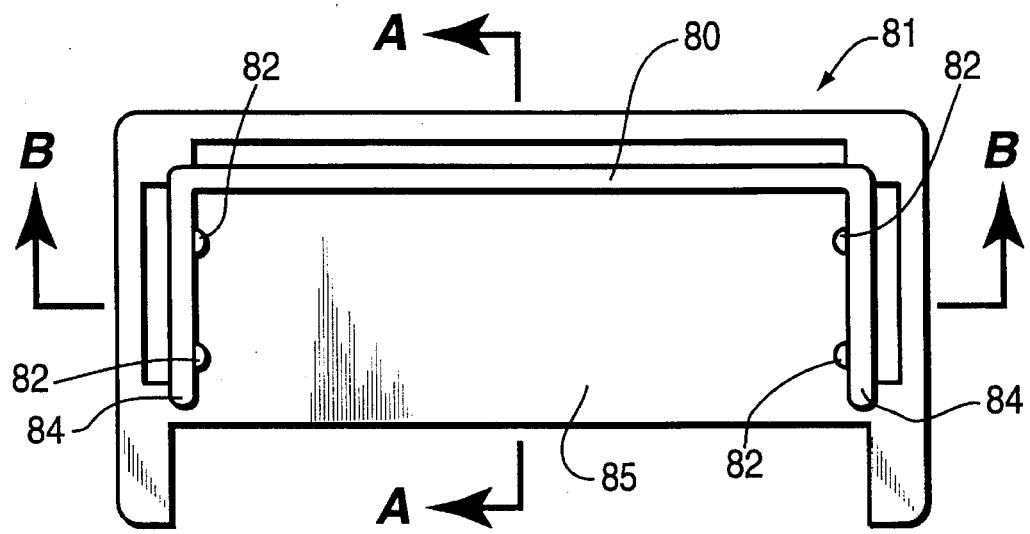
FIG. 20 is a top plan view of a base unit of a cartridge.
Figure 21:
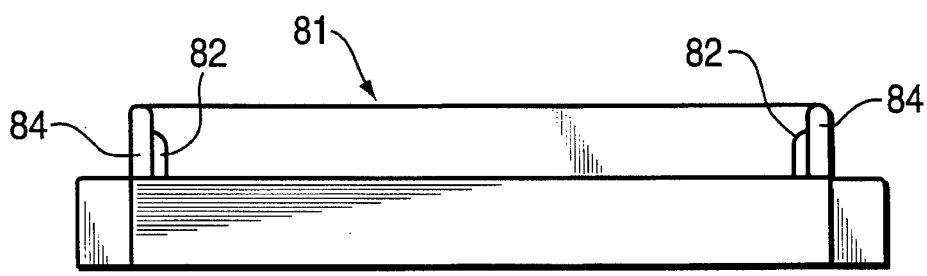
FIG. 21 is a front elevational view of the base unit of FIG. 20.
Figure 25:
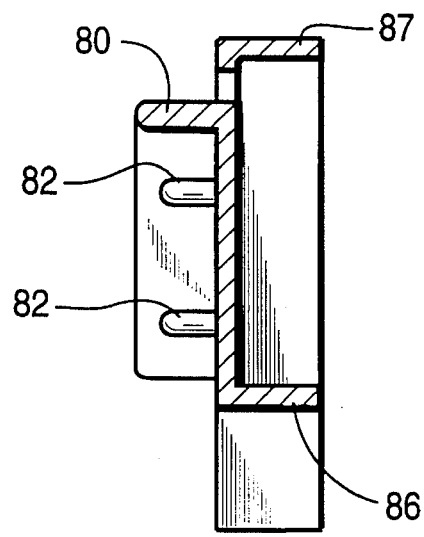
FIG. 25 is a cross-sectional view of the base unit of FIG. 20 taken along the A—A axis of FIG. 20.
Figure 26:
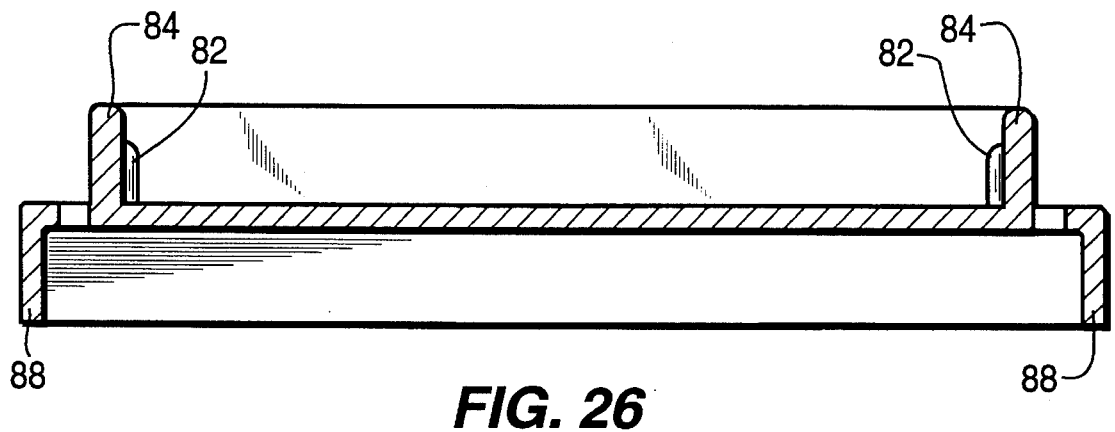
FIG. 26 is a cross-sectional view of the base unit of FIG. 20 taken along the B—B axis of FIG. 22.

The back electrode assembly alignment wall (80); denoted in FIGS. 20 and 25 of the base unit fits snugly against the back edge (4); denoted in FIGS. 27 and 30 of the electrode assembly. Similarly, the nubs (82) on the side alignment walls (84); denoted in FIGS. 20, 21 and 26 fit snugly against the sides (7) of the electrode assembly. As a result, the back electrode alignment wall and the nubs (and the side electrode alignment walls) define precisely the position of the electrode assembly as regards the base unit and therefore as regards the remainder of the entire cartridge. (See, for example, FIG. 19.)

Figure 15:
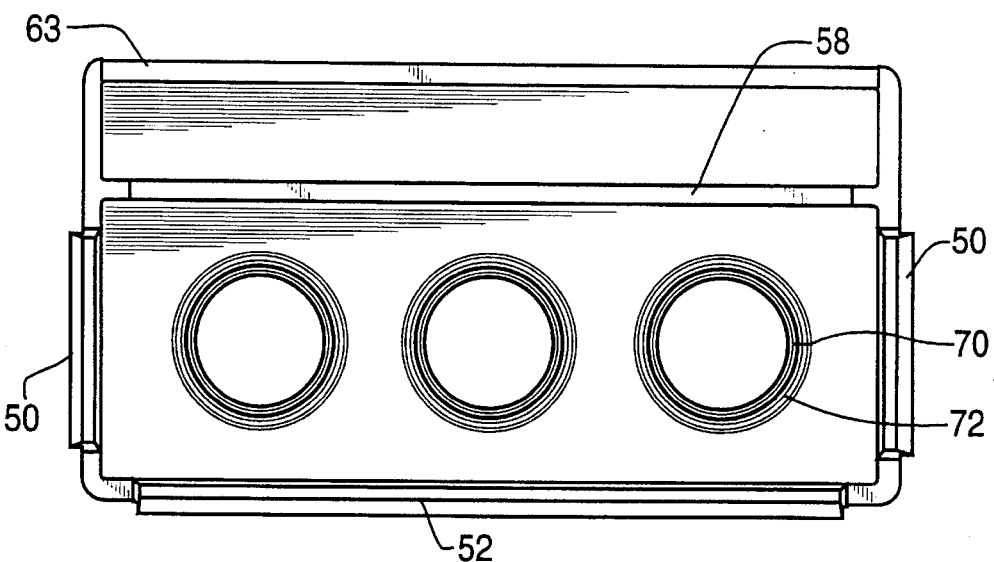
FIG. 15 is bottom plan view of the cover unit of FIG. 11.
Figure 16:
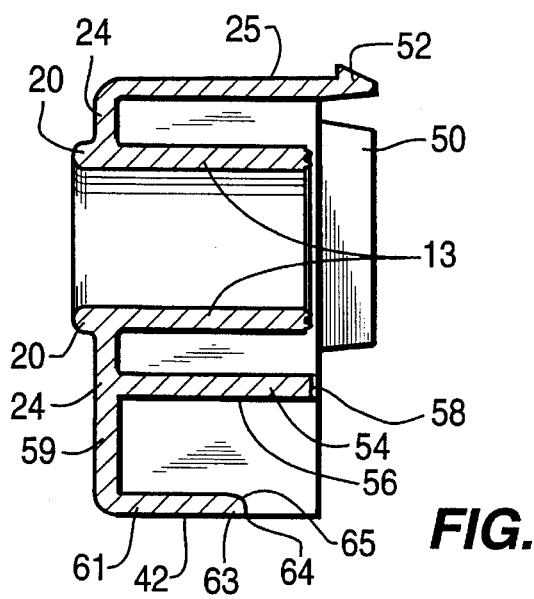
FIG. 16 is a cross-sectional view of the cover unit of FIG. 11 taken along the A—A axis of FIG. 7.
Figure 17:
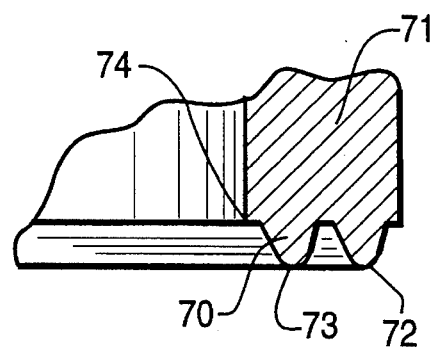
FIG. 17 is a detail of the lower edge of a cylinder rim.
Figure 18:
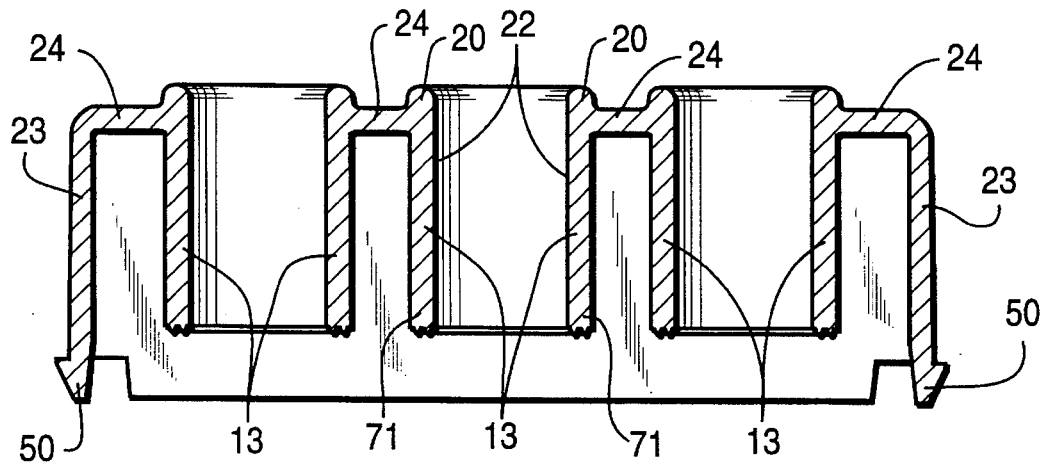
FIG. 18 is a cross-sectional view of the cover unit of FIG. 11 taken along the B—B axis of FIG. 11.

The cover unit (77) is shown separately in FIGS. 11 through 18. Each inner wall surface (22) defines a hollow cylindrical cavity (14) (See FIG. 11). FIG. 18 illustrates how the roof (24) of the cover unit serves as a means for connecting each cylinder wall (13) to the wall (13) of an adjoining cylinder. Furthermore, the roof (24) serves as a means of connecting two of the cylinder walls (13) to the two side walls (23). Similarly, FIG. 16 shows how the roof (24) of the cover unit serves as a means of connecting the wall (13) of a cylinder to the back wall of the cover unit (25), to the divider wall (54), and to the overhang hanging segment (61). The inner rim (70); denoted in FIGS. 15 and 17 and outer rim (72); denoted in FIGS. 15 and 17 that serve as sealing means and become effective when, in the assembled cartridge, they are forced against the top surface of the electrode assembly due to forces exerted by the securing means (latch means in this example) and transmitted through the sealing means and/or pressure pad. (Alternative sealing means, such as a rubber or foam gasket, or an O ring, are possible. Such sealing means also form pan of the cell wall.) Under the pressure of such forces, the sealing means act to create a leak-proof seal in conjunction with the electrode assembly upper surface. As a result, fluid samples added to the cells will not leak.

Two rims (70 and 72); both denoted in FIGS. 15 and 17 located at the extreme lower end (71); denoted in FIG. 17 of the cylinder wall (13) are a more reliable seal than one such rim. It is possible to have more than two rims; that may require a thicker cylinder wall and would provide more resistance against any forces that tend to pull the electrode assembly out of the cartridge. The base unit is shown separately in FIGS. 20 through 26. The base unit has side electrode assembly alignment walls (84) and a back electrode assembly alignment wall (80); each of those three walls are part of the base unit and serve to align the electrode assembly and pressure pad correctly on the platform. Visible is the platform (85). Also visible are apertures (90) of side latch receiving components and the deformable rectangular perimeters (93) of those apertures. Similarly visible is the aperture (92) of a back latch receiving component and a deformable rectangular perimeter (94) of that aperture. The base unit has, on its underside, support units, in this case both a front support unit (86), a back support unit (87), and side support units (88).

Figure 11:
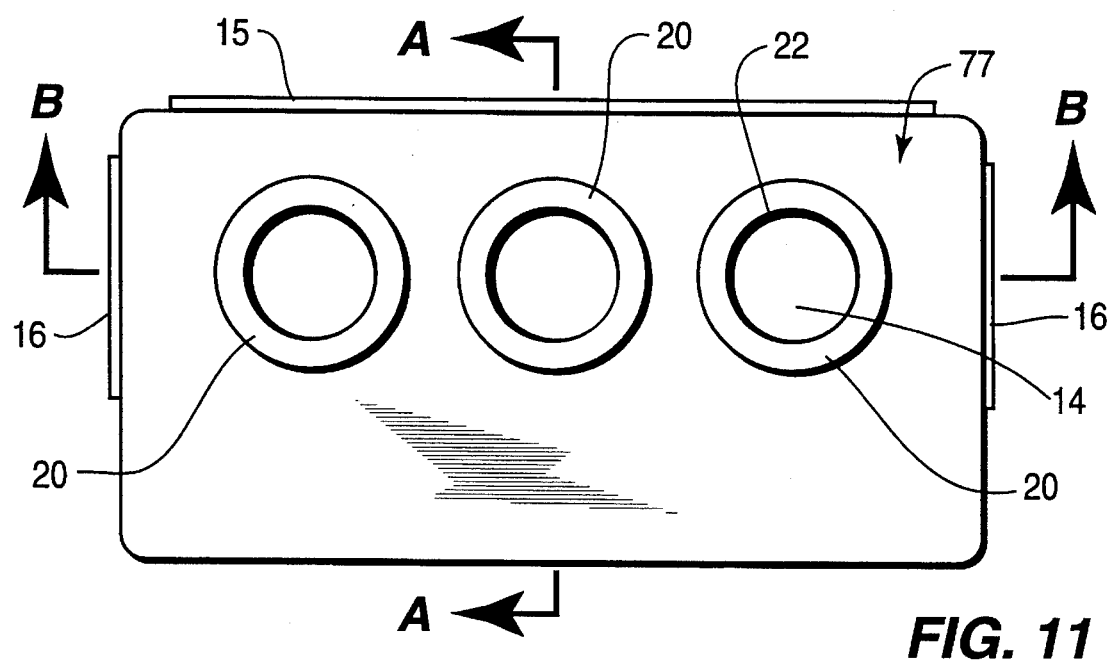
FIG. 11 is a top plan view of a cover unit of a snap-together cartridge.

In FIG. 11, the top surface (16) of latch means on the sides of the cartridge and the top surface (15) of latch means on the back of the cartridge, are visible. FIGS. 9, 10, 16, and 18, latch means protruding components (50, 52) that are part of the cover unit are visible. They each fit through latch receiving means components which in this case are rectangular apertures (90, 92) surrounded by rectangular perimeters (93, 94) in the base unit (see FIG. 24). When the cartridge is assembled, the protruding component will lie under the receiving component. In order for the latch means to be assembled, the deformable rectangular perimeter must be deformed, preferably manually, sufficiently for the latch protruding component to pass through it. This is accomplished by manufacturing the base, and generally the cover unit also, out of a flexible material such as a polyethylene or other plastic. The choice of material or materials for constructing the base and cover units will take into consideration that the inner cell wall should not interfere with the assay for the analyte by emitting undesirable contaminants into the samples or by adsorbing materials out of the sample solution that are supposed to remain in the sample solution for purposes of the assay. The choice of material or materials will also take into consideration that the material should not interfere with the electronic circuits of the cartridge; e.g., by causing a short circuit.

Figure 8:
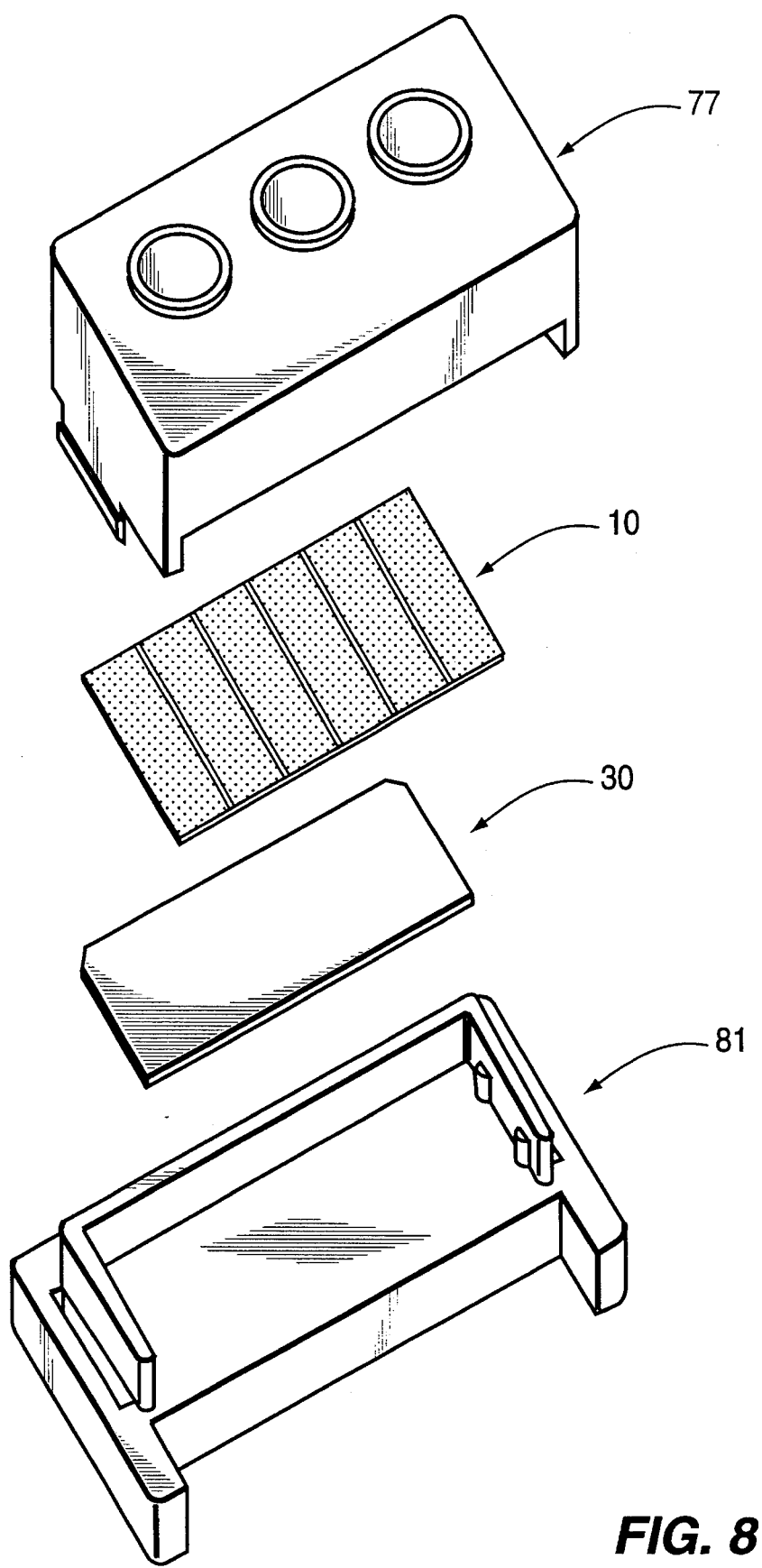
FIG. 8 is an exploded perspective view of the assembled cartridge of FIG. 2.

The pressure pad (e.g., 0.079 cm. thick), (30), made for example of a polyethylene foam (e.g., Volara, grade 060/E00031WH) lies on the platform (85), and increases the pressure between the electrode assembly surface and the rims (70, 72) on the lower edge of the cylinder, thereby insuring that the cell is leakproof (See FIG. 8). Its lower layer, not shown here, is identical to the top layer. However, in assembling the cartridge it is advantageous to coat the underside of the pressure pad with an adhesive. The pressure pad could be replaced by molding the base unit so that its platform (85) is raised slightly in the areas under the cylindrical cells. In the example in the Figures, the pressure pad in the assembled cartridge does not extend past the lower edge (58) of the divider wall.

Assays usable with the cartridge

The cartridge is usable with a wide variety of assays feasible in sensors. The use of sensors for detecting analytes has been disclosed in U.S. Pat. No. 4,560,534 (Kung et al.), U.S. Pat. No. 4,929,313 (Wrighton et al.), and U.S. Pat. No. 4,334,880 (Malmros et al.). It has also been disclosed in European patent documents 193154 (Taniguchi et al..), 467219A2 (Musho et al.), and 314009 (Albarella et al.) as well as numerous other publications and patents. The aforementioned patent publications specifically discuss the use of antibodies on an internal surface of a cell (Malmros, Taniguchi), the use of an enzyme on a cell surface (Albarella), the detection of small ions ($H^+$, $Li^+$, and others; Wrighton), and enzymatic reactions that generate the dopant, $I_3^-$ (Musho).

Coated Electrode and Cartridge Assembly

Dimensions denoted in this application are for one preferred embodiment of the cartridge. As will be evident to anyone of ordinary skill in the art, a wide variety of dimensions are possible for the inventions herein.

In a preferred embodiment, electrode assemblies measuring 2.21 cm×4.38 cm are cut from the sheets and assembled into individual cartridges. The assembly has a set of six metal strips (2.21 cm.×0.679 cm.), and all strips are separated by a fixed spacing (0.0508 cm.) Two narrow strips (2.21 cm.×0.0254 cm.) separate the two outside metal strips from the edges of the electrode assembly. Injection-molded cartridges consisting of two-piece parts (cover unit and base unit) have been designed for ease of mold manufacture and optimization of electrode surface area. The dimensions are chosen for compatibility with standard electrical connectors. For cartridge assembly, an electrode set is aligned in the base unit to registration posts, and the cover unit is snapped in place over the electrode set. The cover unit has three cells; each cell in the preferred embodiment is defined by a 1.52 cm deep hollow cylinder seated on the electrode assembly and centered on one of the three electrode pairs. The separation between the axes of symmetry of two adjacent cylindrical cells is 1.461 cm.

Electronic Instrumentation Unit and User Interface

The use of an electronic instrumentation unit to measure changes in electrical resistance, capacitance, field strength, ionic impedence, or solution impedence, is well known in the art. The use of an electronic instrumentation unit to compare any of those variables in two or more elements is also well known in the art.

A conductivity-measuring instrumentation unit can be used either as a stand-alone unit in the field for immediate results or connected to a personal computer for more intensive data handling. The unit includes all supporting electronics and hardware, such as rechargeable batteries, dc-recharge plug, ac-to-dc adaptor, measurement circuitry with data storage, and an RS232 port to interface a computer or printer with the measurement electronics. To make electrical connection between the cartridge and the measurement electronics, a docking station is provided directly on the instrumentation unit.

As with most electrode-electrolyte systems, there are resistive and capacitive components in the impedance. Changes in the polymer electrical properties due to doping are typically associated with the resistive components; however, both resistive and capacitive components are affected by the doping process. A measurement system that monitors and analyzes these components can be incorporated into the electronics. A data-base for film electrical properties can be established and used to evaluate the specifications of a given sensor prior to and during use.

What is claimed is:

1. An electrochemical sensor cartridge comprising an electrode assembly and at least three hollow cells, said electrode assembly being a thin flexible film that comprises (1) a first layer that is nonconducting, (2) a second layer that is a layer of metal electrodes said metal electrodes accessible to electrical contacts external to the cartridge, and (3) a third layer comprising an electroactive polymer film, said first layer below said second layer, said third layer above said second layer, wherein each hollow cell is comprised of a cell floor and a cell wall with a lower rim, wherein each cell floor is a portion of the top surface of said electrode assembly, and wherein each said lower rim is in leakproof contact with the outer perimeter of a cell floor, wherein the cartridge is constructed from a set of parts that comprises a cover unit, a base unit, and said electrode assembly, such that the electrode assembly in the cartridge is sandwiched between the cover unit and the base unit, and wherein the cover unit and base unit are attached to each other by a securing means, and wherein the three hollow cells are in a linear array.

2. An electrochemical sensor of claim 1 wherein each hollow cell is cylindrical in shape.

3. A cartridge of claim 2 that further comprises an overhang or canopy that covers an area above the access electrodes to prevent a drop of fluid from inadvertently falling onto the access electrodes.

4. The cartridge of claim 3 wherein the overhang has a lower segment with a front edge that is sharp and a back edge that is rounded so that a drop falling from that lower segment will fall from the sharp edge as opposed to the rounded edge and therefore not touch the electrode assembly when that assembly is in a horizontal plane.

5. An electrochemical sensor of claim 1 wherein all the cells are in a linear array.

6. An electrochemical sensor of claim 5 wherein there are three cells in a linear array.

7. An electrochemical sensor of claim 1 wherein at least three hollow cells are in a linear array parallel to a linear array of access electrodes that are electrically connected to said cells.

8. An electrochemical sensor of claim 1 wherein the three hollow cells are in a linear array parallel to a linear array of electrodes that are electrically connected to said cells.

9. A cartridge of claim 1 that covers an area above the access electrodes to prevent a drop of fluid from inadvertently falling onto the access electrodes.

10. The cartridge of claim 9 wherein the overhang has a lower segment with a front edge that is sharp and a back edge that is rounded so that a drop falling from that lower segment will fall from the sharp edge as opposed to the rounded edge and therefore not touch the electrode assembly when that assembly is in a horizontal plane.

11. A cartridge of claim 1 wherein the second layer of the electrode assembly comprises a set of parallel metal strips, each metal strip separated from the others, each metal strip comprising a first region that serves as a cell electrode, a second region that serves as a connector, a third that serves as an access electrode, the first region contiguous with the second region, the second region contiguous with the third region.

12. An electrochemical sensor of claim 11 wherein each hollow cell is cylindrical in shape.

13. An electrochemical sensor of claim 11 wherein the three hollow cells are in a linear array parallel to a linear array of access electrodes that are electrically connected to said cells.

14. A cartridge of claim 11 that further comprises an overhang or canopy that covers an area above the access electrodes so as to prevent a drop of fluid from inadvertently falling onto the access electrodes.

15. The cartridge of claim 14 wherein the overhang has a lower segment with a front edge that is sharp and a back edge that is rounded so that a drop falling from that lower segment will fall from the sharp edge as opposed to the rounded edge and therefore not touch the electrode assembly when that assembly is in a horizontal plane.

16. An electrochemical sensor cartridge of claim 1 wherein the electroactive polymer is selected from the group consisting of polyacetylene, polypyrrole, polythiophene, poly(3-alkylthiophene), polyphenylene sulfide, polyphenylene vinylene, polythienylene vinylene, polyphenylene, polyisothanonaphthene, polyazulene, polyfuran, polyanaline, and a derivative thereof.

17. An electrochemical sensor of claim 1 wherein the securing means is a screw or a latch.

18. An electrochemical sensor of claim 1 wherein the securing means is a latch.

* * * * *